(12) United States Patent
Kakar

(10) Patent No.: US 7,354,609 B1
(45) Date of Patent: Apr. 8, 2008

(54) MEDICATION FOR HYPERACIDITY

(76) Inventor: Sharwan Kumar Kakar, 37 June Ave., Bayville, NY (US) 11709

( * ) Notice: Subject to any disclaimer, the term of this patent is extended or adjusted under 35 U.S.C. 154(b) by 0 days.

(21) Appl. No.: 11/357,536

(22) Filed: Feb. 21, 2006

Related U.S. Application Data

(63) Continuation-in-part of application No. 10/246,403, filed on Sep. 18, 2002, now abandoned, which is a continuation-in-part of application No. 09/649,034, filed on Aug. 25, 2000, now abandoned, which is a continuation of application No. 08/990,993, filed on Dec. 15, 1997, now abandoned.

(51) Int. Cl.
*A61K 36/78* (2006.01)
(52) U.S. Cl. .................................. 424/757
(58) Field of Classification Search ............... None
See application file for complete search history.

(56) References Cited

U.S. PATENT DOCUMENTS 3,253,988 A * 5/1966 Scott .................. 424/653
4,029,773 A * 6/1977 Beigler et al. ............ 514/53
4,439,419 A * 3/1984 Vecchio .................. 424/78.1
5,068,109 A * 11/1991 Foldager et al. .......... 424/441

FOREIGN PATENT DOCUMENTS

JP 01216936 A * 8/1989
WO WO 95/10290 * 4/1995

OTHER PUBLICATIONS meridianinstitute.com/ccsi/scale4.*

* cited by examiner

*Primary Examiner*—Christopher R. Tate
*Assistant Examiner*—Melenie McCormick

(57) ABSTRACT

A medication for hyperacidity is provided and consists of seven ingredients to bring about improvements in a patient with hyperacidity. The ingredients are soybeans, vegetables, milk, butter fats, whole wheat, fruits and magnesium citrate.

1 Claim, No Drawings

MEDICATION FOR HYPERACIDITY

CROSS REFERENCE TO RELATED APPLICATION

The present application is an amendment of U.S. application Ser. No. 11/357,536, filed Feb. 21, 2006, and entitled "Medication for Hyperacidity", the entire contents and disclosure of which are hereby specifically incorporated by reference. Said U.S. application Ser. No. 11/357,536 is a CIP of U.S. application Ser. No. 10/246,403, filed Sep. 18, 2002, now abandoned and entitled "Cytogenic/Nucleogenic Healing", the entire contents and disclosure of which are specifically incorporated by reference. Said U.S. Ser. No. 10/246,403 is a CIP of U.S. application Ser. No. 09/649,034, filed Aug. 25, 2000, now abandoned and entitled "Cytogenic/Nucleogenic Healing" which is a CON of U.S. application Ser. No. 08/990,993, filed Dec. 15, 1997, now abandoned and entitled "Cytogenic/Nucleogenic Healing", the entire contents and the disclosure of which are hereby specifically incorporated by reference.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of Invention

The present invention pertains to hyperacidity and more specifically it relates to a medication for treating hyperacidity in the stomach.

The medical term for hyperacidity is gastro-esophageal reflux disease. Chronic irritation or regurgitation of gastric acid may interfere with esophageal function and lead to regurgitation of previously swallowed materials. In extreme case excess acid may cause ulceration of gastric lining leading to peptic ulcer.

When one talks of hyperacidity he actually means excess acid in the stomach. In chemical terms hyperacidity means excess of hydrogen ion concentration. Minor changes in hydrogen ion concentration from the normal value can bring profound alteration in the body. For this reason the regulation of hydrogen ion concentration is one of the most important aspects not only for digestive processes but also for the whole body. The symbol pH is normally used to express hydrogen ion concentration. Lower pH corresponds to a high hydrogen ion concentration, which is called acidosis. Since the normal pH of blood is 7.4, an individual with pH below this level is considered to have acidosis, and value above this is considered alkalosis. Rapid rates of metabolism in cells lead to the production of carbon dioxide which lowers pH as seen in patients with diabetes mellitus. Acid-base balance in the body are strictly controlled by various mechanisms and are well expressed in the Henderson-Hasselbalch equation.

The large number of the illnesses patients complain about, are the disorders of the stomach which include nausea, malaise, loss of appetite, depression, abdominal cramps, abdominal pains, gas pains, acidic stomach, heart burns (pyrosis), indigestion or dyspepsia (lack of digestion), acid reflux and peptic ulcers. In many cases heartburns can occur in association with peptic ulcers. Pain in the upper part of abdomen is often caused by peptic ulcer but can also be caused by irritation of lower part of esophagus. During examination patient admits that he has been under stress on his job but his other functions appear to be normal including bowel movement with no loss or gain in weight.

In order to understand hyperacidity, it is essential to know the process of digestion. Gastric acids in association with gastric enzymes play vital role in digestion of various types of foods in the stomach. For instance, the digestion of starch starts in the mouth which is brought about by salivary amylase produced by salivary glands whereas the digestion of proteins starts in the stomach and is brought about by pepsinogen, a gastric substance produced by gastric glands which by action of hydrochloric acid is converted into pepsin. Two other secretions are added into the duodenum, trypsinogen and chemotrypsinogen. The digestion of fats also starts in the duodenum whereas bile mixes with fats and brings about emulsification. Fats are converted into micelles which are thoroughly mixed with aqueous medium. This action of the bile, which contains cholesterol, bile acids and bile salts, is extremely important in the hydrolysis of lipids. The latter is brought about by pancreatic enzymes called lipases. All these broken down substances are absorbed by the intestinal mucosa in form of micelles. Lack of any one of these pancreatic enzymes can lead to severe dyspepsia or indigestion. Indigestion is extremely common and is not considered a serious problem unless it is prolonged for several weeks. It can also be due to irregular meals, excess alcohol intake, ingesting foods which an individual is unaccustomed to.

Hyperacidity can be caused by other factors including stress, infections—latent and/or mutated infections, prescription drugs, hunger pangs or use of specific type of diet over a long period. Other experience symptoms of intolerance and upset stomach to a wide variety of foods including spicy foods, coffee, and dairy products.

Many hypotheses have been proposed for hyperacidity including allergic reaction to food, bacterial infections, hormonal stimulation, nervous impulses, genetic factors, excess bile salt and drugs, but problem remains unresolved. Ulceration in gastric and esophageal linings occurs in patients with decreased mucosal resistance. A variable degree of proliferation is noticeable around the margin of ulcerated site.

2. Description of the Prior Art

A conventional treatment for hyperacidity involves the ingestion of alkali salts. There are an astonishing number of preparations available by prescription or over the counter to relieve the symptoms of nausea, bloated feeling, stomach upset, heartburns, and peptic ulcers including Maalox, Mylanta, Tums, Zantacs and others. Most of the antiacids contain one or two or more of the alkaline salts including sodium bicarbonate, aluminum, calcium and magnesium. Majority of these antiacids are composed of mixtures to counteract side effects caused by either one of them. These antiacids are effective for a short period. They provide a relief for a brief period but the symptoms return after few hours. Prolonged use of these agents can lead to dependency and serious neurological impairments.

There are also antispasmodic drugs that are used as prescription that block the signal to the nervous system, thereby reducing the increased acid secretion. These drugs have side effects of their own including dryness in mouth, blurring of vision, difficulty in urination. Retention of urine may cause prostate problems. In particular, a drug called cimetadine gives some relief to many people with ulcers. But many patients have recurrent problem.

U.S. Pat. No. 5,595,756 discloses liposomal composition encapsulating bioactive agents as antitumor agents having improved circulation longevity. U.S. Pat. No. 5,198,250 entitled "Food and Pharmaceutical Compositions Containing Short Chain Fatty Acids And Methods of Using" discloses methods and compositions to treat atherosclerotic lesions and U.S. Pat. No. 5,214,062 entitled "Methods and Composition for Treating Immune Disorders, Inflammation and Chronic Infections" discloses methods to treat chronic infections. See also U.S. Pat. No. 5,118,673 and U.S. Pat. No. 5,703,060 entitled "Uses of Aloe Products".

PROBLEM TO WHICH THIS INVENTION IS ADDRESSED

Food allergy is an extremely complex and most prevalent problem and is beyond the scope of present invention. Food allergies do persist throughout life. It could be due to genetic or could be familial. It is suffice to say that food intolerance to specific food types can invoke serious to violent antigen-antibody immune response (anaphylactic attack) in some individuals that may prove to be fatal.

The instant invention addresses the problem of treating hyperacidity in the stomach which emphasizes the interaction of various food ingredients.

The medication described herein is designed for a patient who is accustomed to the food ingredients described in this invention since childhood and does not manifest any allergic response to these ingredients.

SUMMARY OF INVENTION

A primary object of the present invention is to provide a medication for hyperacidity in the stomach that will overcome the shortcomings of the prior art through a more holistic approach which emphasizes the interaction of various food constituents.

Another object is to provide a composition for treating hyperacidity that is composed of seven ingredients which will bring about dramatic improvements in a patient with hyperacidic stomach including decrease in acid reflux, lessening of gastro-esophageal erosion, relief from heart burns and abdominal cramps, lessening of anxiety, lessening of depression and improved appetite with restful night sleep.

An additional object is provide a composition that is simple and easy to use.

Further objects of the invention will appear as the description proceeds.

To the accomplishment of the above and related objects, attention being called to the fact that changes may be made in the specific construction described within the scope of the appended claim.

DETAILED DESCRIPTION OF THE PREFERRED EMBODIMENTS

A detailed description will hereinafter be given of the present invention being a medication for the treatment of hyperacidity in the stomach of a human which consists of 25 g. soybeans, 10 g. chopped vegetables, 15 g. milk, 30 g. butter fats, 15 g. whole wheat, 4.995 g. fruits and 0.005 g. magnesium citrate. (These are the suggested dosages for a less seriously ill patient. For an advanced case the concentration of magnesium citrate may be slightly increased to 0.007 g.). This medication is based on dry weight basis. The best way to administer the medication is in form of soup at least three or four times a day at a rate of 1.0-2.0 g./kg./day.

The term "vegetables used herein means species of plants that include algae, alfalfa, artichoke, asparagus, beets, bamboo, broccoli, Brussels sprouts, celery, chicory, cabbage, cauliflower, garlic, green beans, carrot, chick peas, chives, cucumber, egg plant, flax, ginger, gourd, luffa, onion, horse radish, mustard, okra, olive, papaya, peas, pepper, radish, spinach, turnip, tomato, squash, pumpkin, zucchini, anise, basil, coriander, fennel, pepper grass and parsley. This provides chloroplast and protein. The term "fruits" as used herein includes apple, apricot, avocado, banana, blueberry, cantaloupe, cherry, cranberry, currant, gooseberry, grapes, grape fruit, guava, litchi, lime, lemon, mango, orange, peach, pineapple, quince, raspberry, and strawberry with high contents of terpenes, saccharides, polysaccharides and citric acid cycle products.

To prepare and administer the medication for hyperacidity the following steps were taken:

1. Soybeans and whole wheat were cooked in a pan with 1.5 liters of water for 25 minutes at medium heat.

2. To this, finely chopped vegetables, butter fats and milk were added. This mixture was boiled for 10 minutes.

3. The cooked mixture was stirred with fruits and magnesium citrate in a blender.

4. The stirred mixture was made just salty enough to suit patient's taste prior to ingestion.

5. Give a cup of freshly prepared soup in the morning as breakfast to a person with hyper-acidic stomach.

6. Give the rest of soup after every three hours during rest of the day.

Amelioration of symptoms will occur within seventy two hours and apparently will endure as long as the formula is taken. When the treatment is suspended, deterioration will resume after a week or two.

It may take three to four weeks before noticeable improvements take place. The positive changes are decrease in acid reflux, lessening of gastro-esophageal erosion, relief from heartburns and abdominal cramps, lessening of anxiety, lessening of depression and improved appetite with restful night sleep.

It will be understood that each of the elements described above, or two or more together, may also find a useful application in other types of methods differing from the type described above.

While certain novel features of this invention have been described and are pointed out in the annexed claims, it is not intended to be limited to the details above, since it will be understood that various omissions, modifications, substitutions, and changes in the forms and details of the invention and in its operation can be made by those skilled in the art without departing in any way from the spirit and the scope of the of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention. It is therefore intended that such changes and modifications be covered by the appended claims.

What is claimed is new and desired to be protected by Letters Patent is set forth in the appended claims:

1. A method of preparing and administering a medication for the treatment of hyperacidity in the stomach of a human comprising the steps of:

administering to the human a soup formulation which comprises 25 g. soybeans, 10 g. chopped vegetables, 15 g. milk, 30 g. butter fats, 15 g. whole wheat, 4.995 g. fruits and 0.005 g. magnesium citrate; whereby the soup formulation is prepared by:

(a) cooking the soybeans and whole wheat in a pan with 1.5 liters of water for 25 minutes at medium heat;

(b) adding the finely chopped vegetables, butter fats and milk thereto to form a mixture; boiling the mixture for 10 minutes and then allowing it to cool;

(c) stirring the cooked mixture and adding the fruits and magnesium citrate there to in a blender;

(d) optionally adding salt to the blended mixture in an amount salty enough to suit the human's taste prior to ingestion;

(e) giving a cup of the soup formulation in the morning to the human with a hyper-acidic stomach; and (f) giving a cup of the soup formulation to the human every three hours during the rest of the day.

* * * * *